(12) United States Patent
Kim et al.

(10) Patent No.: US 9,539,213 B2
(45) Date of Patent: Jan. 10, 2017

(54) METHOD OF PREPARING MICROSPHERES BY USING POLYMER HAVING SOL-GEL TRANSITION PROPERTY AND MICROSPHERES PREPARED THEREBY

(71) Applicant: CJ CHEILJEDANG CORPORATION, Seoul (KR)

(72) Inventors: Yi Mi Kim, Gyeonggi-do (KR); Young Joon Park, Seoul (KR); Seung Hee Baek, Gyeonggi-do (KR); Sun Kyung Lim, Gyeonggi-do (KR)

(73) Assignee: CJ HEALTHCARE CORPORATION, Seoul (KR)

( * ) Notice: Subject to any disclaimer, the term of this patent is extended or adjusted under 35 U.S.C. 154(b) by 0 days.

(21) Appl. No.: 14/220,875

(22) Filed: Mar. 20, 2014

(65) Prior Publication Data

US 2014/0287045 A1  Sep. 25, 2014

(30) Foreign Application Priority Data

Mar. 20, 2013 (KR) .................. 10-2013-0029999

(51) Int. Cl.
*A61K 9/16* (2006.01)
*A61K 38/09* (2006.01)

(52) U.S. Cl.
CPC .......... *A61K 9/1652* (2013.01); *A61K 9/1641* (2013.01); *A61K 9/1647* (2013.01); *A61K 9/1694* (2013.01); *A61K 38/09* (2013.01)

(58) Field of Classification Search
None
See application file for complete search history.

(56) References Cited

U.S. PATENT DOCUMENTS

| 4,460,563 | A | 7/1984 | Calanchi |
| 4,652,441 | A | 3/1987 | Okada et al. |
| 5,330,767 | A | 7/1994 | Yamamoto et al. |
| 6,020,004 | A | 2/2000 | Shah |
| 6,565,777 | B2 | 5/2003 | Farrar et al. |
| 7,029,700 | B2 | 4/2006 | Mathiowitz et al. |
| 2002/0182412 | A1 | 12/2002 | Farrar et al. |
| 2012/0288434 | A1 | 11/2012 | Yang et al. |

FOREIGN PATENT DOCUMENTS

| JP | 62-201816 A | 9/1987 |
| JP | 2002-514590 A | 5/2002 |
| KR | 10-2011-0044192 A | 4/2011 |
| WO | 98/52547 A1 | 11/1998 |
| WO | 2012/087051 A2 | 6/2012 |

OTHER PUBLICATIONS

Woo et al. Journal of Controlled Release. 75 (2001) 307-315.*
Kwon et al., "Biodegradable Triblock Copolymer Microspheres Based On Thermosensitive Sol-Gel Transition," *Pharmaceutical Research* 21(2):339-343 (Feb. 2004).
Leo et al., "PLA-microparticles formulated by means a thermoreversible gel able to modify protein encapsulation and release without being co-encapsulated," *International Journal of Pharmaceutics* 323:131-138 (2006).
English Translation of Chinese Office Action for corresponding Chinese Patent Application No. 2014101065484 (8 pages) dated Jan. 4, 2016.

* cited by examiner

*Primary Examiner* — Amber D Steele
*Assistant Examiner* — Schuyler Milton
(74) *Attorney, Agent, or Firm* — Seed IP Law Group LLP (57) ABSTRACT

The present invention relates to a method of preparing microspheres by using a polymer having a sol-gel transition property and microspheres prepared thereby, and more particularly, to a method of preparing microspheres by using a polymer having a sol-gel transition property and microspheres prepared thereby capable of preventing a solvent in a polymer solution for a carrier from being rapidly diffused to the aqueous medium before formation of the microspheres to reduce porosity of the microspheres and reduce surface roughness of the microspheres in order to obtain microspheres having a sphere shape, and increasing an encapsulation ratio of a bioactive substance, by using a polymer having a sol-gel transition property as a surfactant included in an aqueous medium into which a primary emulsion is injected and gelating a secondary emulsion formed after injecting the primary emulsion using the sol-gel transition property of the polymer used as the surfactant.

11 Claims, 2 Drawing Sheets

METHOD OF PREPARING MICROSPHERES BY USING POLYMER HAVING SOL-GEL TRANSITION PROPERTY AND MICROSPHERES PREPARED THEREBY

TECHNICAL FIELD

The present invention relates to a method of preparing microspheres by using a polymer having a sol-gel transition property and microspheres prepared thereby, and more particularly, to a method of preparing microspheres by using a polymer having a sol-gel transition property and microspheres prepared thereby capable of preventing a solvent in a polymer solution for a carrier from being rapidly diffused to the aqueous medium during formation of the microspheres to reduce porosity of the microspheres and reduce surface roughness of the microspheres in order to obtain microspheres having a sphere shape, and to increase an encapsulation ratio of a bioactive substance by using a polymer having a sol-gel transition property as a surfactant included in an aqueous medium into which a primary emulsion is injected and gelating a secondary emulsion formed after injecting the primary emulsion using the sol-gel transition property of the polymer used as the surfactant.

BACKGROUND ART

As particle preparation techniques, general preparation methods include a double emulsion method (W/O/W), a phase separation method, a spray drying method, a super critical fluid (SCF) method, and the like. In recent years, a method of preparing monodispersed particles has been developed by which uniform particles can be prepared.

A representative example of the double emulsion method includes a method of preparing fine particles, which includes forming a primary emulsion by dissolving a biodegradable carrier in a solvent and dissolving a water-soluble drug in an aqueous phase, and then forming particles by injecting the primary emulsion into a secondary solution in which poly (vinyl alcohol) (PVA) is dissolved. Takeda corporation registered patent (U.S. Pat. No. 4,652,441) regarding the double emulsion method, and many other patents were filed regarding the double emulsion method after mass production and commercialization. Particularly, methods have been developed of preparing fine particles whose encapsulation ratio is improved according to a drug and which exhibit initial release control by optimizing the composition, molecular weight, change in terminal group, and the like of a polymer configuring the fine particles, and have been known as the most suitable methods up to for the purposes of encapsulating the water-soluble drug. However, as disadvantages, the particles exhibit porosity due to temperature, concentration, and stirring speed during the preparation process, which leads to an increase in the initial drug release ratio and a decrease in the encapsulation ratio of the drug. Further, as a solvent dissolving the polymer, methylene chloride having high toxicity is used, and its water solubility is as low as 20 g/L (20° C.). Since an organic solvent having low water solubility needs to be used to encapsulate the water-soluble drug effectively, solvents that may be selected for dissolving the polymer are limited.

With respect to the phase separation method, a patent (U.S. Pat. No. 4,460,563) was first filed in 1984, and its related products includes Somatuline LA. The phase separation method is a preparation method including forming the primary emulsion into a coacervate with silicon oil and the like and then forming particles by curing the polymer. In recent years, a technical trend of the phase separation method is to control the particle size, encapsulation ratio, and the like of the fine particles according to changes in pH, temperature, and compositions of the coacervate. The phase separation method has an advantage in that the size of the particles may be controlled only by controlling a chemical composition without any need for specialized facilities. However, it has a disadvantage in that a large amount of solvent needs to be used, and it has many parameters when the coacervate is formed.

The spray drying method is a method of forming fine particles by spraying a primary emulsion in hot air. A method was developed by Alkermes Corporation in which the primary emulsion is sprayed in hot air to compensate for the disadvantage that there is a limitation in use of encapsulated drugs, quenched using LN2, and extracted with ethanol. After development of the freeze-spray drying method, similar techniques have been developed so far. Various shapes of spray nozzles have been developed, and fine and uniform particles may also be formed using an atomizer, an electrode, a sonicator, and the like. The spray drying method has an advantage in that the particles may be easily mass-produced, but has a disadvantage that it is difficult to form spherical particles and the primary emulsion needs to be sprayed in hot air except in the freeze-spray drying method.

The super critical fluid (SCF) extraction method is a technique of spraying the primary emulsion with a super critical fluid by using a representative supercritical fluid $CO_2$ as an anti-solvent. The SCF extraction method has an advantage in that it is eco-friendly and does not require an additional process of removing a residual solvent and the like, but has a disadvantage in that it is difficult to control particle size distribution during mass production.

When the particles are prepared using a conventional double emulsion method, the step of forming particles by injecting the primary emulsion into the aqueous medium and diffusing the solvent used in the primary emulsion into the aqueous medium is very important in preparing the particles. In the step, particle size, porosity, surface roughness, encapsulation ratio, and the like of the fine particles are determined according to the speed of the solvent which is diffused into the aqueous medium. The solvent diffusion speed is determined according to the kind of solvent, water-solubility of the solvent, temperature of the aqueous medium, and the kind, concentration, stirring speed, and the like of a surfactant configuring the aqueous medium.

In the above step, in order to increase the speed at which the solvent is diffused into the aqueous medium, a method of selecting a solvent having high water-solubility, increasing a temperature of the aqueous medium, reducing a concentration of the surfactant configuring the aqueous medium, or the like may be used. When the solvent diffusion speed is increased, the curing time of the polymer constituting the carrier is shortened, and thus the porosity of the particles is increased, the particle size is relatively large, and the encapsulation ratio is decreased. As a result, a solvent having high water-solubility such as ethyl acetate is diffused into the aqueous medium at a rapid speed, resulting in difficulty in forming a spherical shape, a low encapsulation ratio, and easily-formed porous particles. Accordingly, when the solvent having high water-solubility is used, the concentration of the aqueous medium is increased or the temperature is decreased to prevent the solvent from being diffused to the aqueous medium at a rapid speed. In U.S. Pat. No. 6,565,777, a multistep method of preparing fine particles using ethyl acetate is disclosed. This is a method of forming particles by initially reducing the volume of the aqueous medium to prevent ethyl acetate from being diffused into the aqueous medium at a rapid speed before forming the fine particles, and then evaporating the residual solvent by diluting the particles with a large amount of aqueous medium. However, it is disadvantageous in that a yield is reduced to 10 to 20%. Accordingly, in order to form the particles by various methods without limiting the solvent, the demand for a technique capable of controlling solvent diffusion time is very high.

In order to cure the polymer and diffuse the solvent into the aqueous medium, generally, a stirring process is performed. The stirring process includes methods such as stirring at room temperature, heated stirring, pressure stirring, and the like. In the case of stirring at room temperature, stirring time during mass production is increased, and a water-soluble drug is released after stirring for a long time, which leads to a decrease in the encapsulation ratio. During heated stirring, the curing speed of the polymer is increased and the stirring time is reduced, but the polymer exhibits porosity and its content is decreased. During pressure stirring, the solvent is diffused into the aqueous medium and simultaneously evaporated by pressure, and thus the solvent may be evaporated in a rapid time, and fine particles appropriate under the guidelines on residual solvents in pharmaceuticals may be prepared. However, during pressure stirring, when the reaction volume is large, it is difficult to reach a desired vacuum and the degree of vacuum is decreased, and the polymer needs to be carefully treated to prevent formation of bubbles in the solvent during stirring under the control of the vacuum. Particularly, when the surfactant is included, the bubbling phenomenon is more serious, and thus conditions need to be maintained to control a vacuum pressure. In order to solve these problems, in U.S. Pat. No. 7,029,700, a method of cooling the entire aqueous medium and removing the solvent under depressurization was used. Further, in U.S. Pat. No. 6,020,004, a preparation method of obtaining microspheres by cooling and freeze-drying the primary emulsion was disclosed.

Under the background, the present inventors have confirmed that microspheres having a spherical shape may be obtained by using a polymer having a sol-gel transition property as a surfactant included in an aqueous medium into which a primary emulsion is injected in order to gelate a secondary emulsion formed after injecting the primary emulsion, thereby preventing a solvent in a polymer solution for a carrier from being rapidly diffused into the aqueous medium during formation of the microspheres to reduce porosity of the microspheres and reduce surface roughness of the microspheres, and a high encapsulation ratio of the microspheres may also be easily achieved without restriction to solvent selection, or other stirring or solvent evaporation. Therefore, the present invention has been completed based on these facts. Further, in the method of preparing microspheres according to the present invention, since a desired amount of microspheres may be obtained at a low volume ratio of the secondary emulsion to the primary emulsion, innovative process efficiency may be improved through reduction of the reaction volume.

DISCLOSURE

Technical Problem

An object of the present invention is to provide a method of preparing microspheres capable of obtaining fine particles having a spherical shape, and increasing an encapsulation ratio of a bioactive substance.

Another object of the present invention is to provide microspheres prepared by the preparation method.

Yet another object of the present invention is to provide a drug delivery system containing the microspheres as an active component.

Technical Solution

In order to solve the prior-art problems, the present invention provides a method of preparing microspheres in which a bioactive substance is encapsulated in a polymer for a carrier. Here, the method includes the following steps:

1) forming a secondary emulsion by injecting a primary emulsion, in which the bioactive substance and the polymer for a carrier are mixed, into an aqueous medium in which a polymer having a sol-gel transition property is dissolved (Step 1); and 2) performing a gelation reaction on the secondary emulsion (Step 2).

Preferably, the method of preparing microspheres may further include removing a residual solvent and an aqueous medium and collecting the microspheres after Step 2) (Step 3).

The present invention is characterized in that a solvent in a polymer solution for a carrier may be prevented from being rapidly diffused to the aqueous medium during formation of the microspheres to reduce porosity of the microspheres and reduce surface roughness of the microspheres in order to obtain microspheres having a sphere shape, and an encapsulation ratio of a bioactive substance may be increased, by using a polymer having a sol-gel transition property as a surfactant included in an aqueous medium into which a primary emulsion is injected and gelating a secondary emulsion formed after injecting the primary emulsion using the sol-gel transition property of the polymer used as the surfactant.

Further, the present invention has an effect that there is no limitation to the solvent because any solvent having high water solubility is usable using a method of gelating the secondary emulsion as described above.

Further, the present invention is characterized in that the residual solvent and the aqueous medium may be removed at a rapid speed by completely evaporating the residual solvent and the aqueous medium, for example, using a vacuum drying method and the like, without a stirring process during the step of removing the residual solvent and the aqueous medium after gelation, and the aqueous medium itself may be optionally used by completely drying the aqueous medium without a washing process.

Furthermore, since the solvent is evaporated at a rapid speed without stirring, an excellent encapsulation ratio can be achieved in spite of the small reaction volume. Due to a significant reduction in reaction volume, the present invention can be easily applicable to mass production.

Further, the present invention has an effect of controlling the size of particles by controlling a concentration of a surfactant polymer having a sol-gel transition property included in the aqueous medium.

As the step of forming the secondary emulsion by injecting the primary emulsion, in which the bioactive substance and the polymer for the carrier are mixed, into the aqueous medium in which the polymer having the sol-gel transition property is dissolved, Step 1 is to form the secondary emulsion by injecting the primary emulsion including the bioactive substance and the polymer for the carrier into the solution in which the polymer having the sol-gel transition property as a surfactant is dissolved in the aqueous medium.

The term "bioactive substance" used in the present invention means a material serving to rectify an abnormal condition caused due to deficiency or excessive secretion of a material involved in functional regulation in vivo, as a material of improving or suppressing the functions of a living body when organisms manage their lives.

In the present invention, the bioactive substance may be at least one selected from the group consisting of luteinizing hormone-release hormone (LHRH) homologs, peptides, and salts thereof. In detail, among the bioactive substances, goserelin, leuprolide acetate, triptorelin, buserelin, nafarelin, and the like may be used as an agonist of the LHRH homologs, and cetrorelix, argitide, and the like may be used as an antagonist. In addition, both water-soluble and water-insoluble drugs such as proteins, DNA, and chemical drugs may be used as the bioactive substance without limitation. Further, the bioactive substances may be used either alone or in combination of two or more thereof.

According to the present invention, since the solvent of the polymer solution for the carrier is controlled to be dispersed into the aqueous medium by the gelation reaction as described above, the kind of solvents used to dissolve the polymer for the carrier is not particularly limited. For example, in the present invention, the primary emulsion may be prepared by dissolving the polymer for the carrier in at least one solvent selected from the group consisting of methylene chloride, chloroform, acetonitrile, dimethylsulfoxide, dimethylformamide, and ethyl acetate, but the present invention is not limited thereto.

The term of the "polymer for the carrier" used in the present invention means a polymer serving to carry the bioactive substance in order to deliver the bioactive substance.

In the present invention, as the polymer for the carrier, general polymers may be used. Preferably, the polymer for the carrier may be a biodegradable polymer. In detail, the polymer for the carrier may be at least one selected from the group consisting of polyester such as polylactide (PLA), polyglycolide (PGA), polylactide-co-glycolide (PLGA), polyorthoester, polyanhydride, polyaminoacid, polyacetal, polycyanoacrylate, polycaprolactone, polydioxanone, polyalkylene alkylate, and the like, but the present is not limited thereto.

In the present invention, examples of the aqueous medium usable in Step 1) may include water, but is not limited to water. For example, all kinds of solvent may be used as long as they can dissolve the drug.

Generally, a surfactant is added into the secondary emulsion for a double emulsion method to facilitate formation of the particles. Most typically, poly(vinyl alcohol) which is a nonionic surfactant may be exemplified. Polysorbate, poloxamer, polyethylene glycol, and the like may be used, but the present invention is not limited thereto. In the present invention, a preparation method was developed, which includes forming particles by using the polymer having the sol-gel transition property as a surfactant instead of a general surfactant and gelating the particles in order to rapidly evaporate the solvent. Generally, when the primary emulsion is injected into the secondary emulsion, the polymer for the carrier is cured at a rapid speed, and a volume of the secondary emulsion need to reach 100 to 200 times or more a volume of the primary emulsion in order to evaporate the solvent. When the volume ratio is low, the curing speed of the polymer for the carrier is decreased, and encapsulating efficiency of the drug is decreased accordingly. In the present invention, the volume ratio is about 10 to 20 times, but since the secondary emulsion is gelated such that the solvent is evaporated at a rapid speed without stirring, even though the reaction volume is small, the encapsulating efficiency is increased.

The term "polymer having the sol-gel transition property" used in the present invention means a polymer in which a sol state is converted to a gel state by specific stimuli. The specific stimuli may vary according to the kind of polymers, and may, for example, include a change in temperature, a change in pressure, a change in PH, or addition of salts, and the like, but the present invention is not limited thereto.

In the present invention, the polymer having the sol-gel transition property may be used without limitation as long as they can enable the sol-gel transition and facilitate formation of the particles. In detail, the polymer having the sol-gel transition property may be at least one selected from the group consisting of methyl cellulose, hydroxypropylmethylcellulose (HPMC), ethylhydroxyethylcellulose (EHEC), xyloglucan, chitosan, poly(N-isopropylamide) (PNIPAM), poly(N-isopropylamide-co-acrylic acid), poloxamer (PEO-PPO-PEO), Poloxamer-g-PAA, PAA-g-poloxamer, PEO-PLGA-PEO, and poly(vinyl alcohol).

As the step of performing the gelation reaction with respect to the secondary emulsion, Step 2) is to gelate the secondary emulsion in order to reduce diffusion speed of the solvent diffused into the aqueous medium.

In Step 2), solubility of the solvent is rapidly decreased by gelating the secondary emulsion, and thus, the particles may be formed regardless of the kinds of solvents.

In Step 2), the gelation may be properly performed by known methods according to the kind of the polymer having the sol-gel transition property used as described in Step 1). For example, in the case of methyl cellulose, the secondary emulsion may be gelated by adding NaCl at a proper concentration or adding NaCl and heating, and in the case of poloxamer, the secondary emulsion may be gelated by heating preferably at 35 to 50° C., and most preferably 40° C., which varies according to the kind and concentration of poloxamers. Further, in the case of hydroxypropylmethylcellulose (HPMC), ethylhydroxyethylcellulose (EHEC), xyloglucan, chitosan, poly(N-isopropylamide) (PNIPAM), poly(N-isopropylamide-co-acrylic acid), Poloxamer-g-PAA, PAA-g-poloxamer, PEO-PLGA-PEO, and poly(vinyl alcohol), the secondary emulsion may be gelated by heating at a proper concentration for gelation and a proper temperature. In some cases, an additive such as NaCl may be optionally added, and pH may be optionally controlled.

As the step of collecting the microspheres by removing the residual solvent and the aqueous medium, Step 3) is to collect the microspheres by removing the solvent from the gelated material.

Preferably, the removal of the residual solvent and the aqueous medium of Step 3) may be performed using a vacuum drying method. In detail, the vacuum drying method may be performed by evaporating the solvent under a vacuum having a range of 0 to 0.99 Torr.

In Step 3), the residual solvent and the aqueous medium may be removed at a rapid speed by completely evaporating the residual solvent and the aqueous medium using the vacuum drying method, and in some cases, the aqueous medium itself may be used by completely drying the aqueous medium without performing a washing process. As such, according to the preparation method of the present invention, since a stirring process which is generally performed to remove the solvent may be omitted, it is possible to overcome the disadvantages of the double emulsion method in that the encapsulation ratio is decreased due to the release of the encapsulated drug during the stirring process, or the residual solvent remains.

Another advantage of the preparation method according to the present invention is that a solvent which may dissolve the polymer for the carrier forming the microspheres is not limited. When ethyl acetate, acetone, and the like having high miscibility due to the high water solubility are used in the conventional a double emulsion method, spheres may not be formed or the encapsulation ratio may be very low, at less than approximately 50%. Various factors exist as the causes, but, among the causes, this is because the solvent is rapidly diffused into the aqueous medium before the microspheres are formed in a spherical shape. In order to form the spheres and increase the encapsulation ratio, the water solubility of the solvent need to be reduced. In the present invention, the polymer having the sol-gel transition property is dissolved in the aqueous medium at a proper concentration, and the primary emulsion is injected thereto to form a secondary emulsion, and then the secondary emulsion is completely gelated to reduce the solubility of the solvent. By the preparation method, the use of ethyl acetate has an advantage in that the encapsulation ratio is 70 to 100 wt %, and the particles may be uniformly formed at a particle size of 5 to 10 μm.

Further, uniform and small fine particles having a particle size in a range of 1 to 10 μm may be formed by controlling the concentration of the polymer having the sol-gel transition property. Furthermore, when the secondary emulsion is formed, the reaction volume may be significantly reduced to $\frac{1}{10}$ to $\frac{1}{20}$ that of the conventional preparation method, and thus it is very advantageous for mass production.

Further, the present invention provides microspheres in which the bioactive substance is encapsulated in the polymer for the carrier prepared by the method.

That is, the microspheres of the present invention in which the bioactive substance is encapsulated in the polymer for the carrier are formed by emulsifying the polymer for the carrier and the bioactive substance with the polymer having the sol-gel transition property.

Further, the present invention provides a drug delivery system including the microspheres as an active component.

In the present invention, the drug delivery system may include a pharmaceutically acceptable carrier and a pH regulator.

In the present invention, the drug delivery system may be in the form of an injection, but the present invention is not limited thereto.

In the present invention, when the drug delivery system may be in the form of an injection, the pharmaceutically acceptable carrier is water for injection, and the pH regulator may be an acid such as hydrochloric acid, or a base such as sodium hydroxide. In this case, the pH of the injection may be preferably regulated to about 6.0 to 8.0, and more preferably about 7.2 to 7.8.

Further, the present invention provides microspheres in which the bioactive substance is encapsulated in the polymer for the carrier. Here, the microspheres are formed by emulsifying the polymer for the carrier and the bioactive substance by means of the polymer having the sol-gel transition property.

In the present invention, the polymer for the carrier, the bioactive substance, and the polymer having the sol-gel transition property may be described in the same manner as in the method of preparing microspheres.

Effects of the Invention

According to the present invention, the solvent of the polymer solution for the carrier can be prevented from being rapidly diffused in the aqueous medium before formation of the microspheres to reduce porosity of the microspheres and reduce surface roughness of the microspheres in order to obtain microspheres having a sphere shape, and an encapsulation ratio of a bioactive substance may be increased by injecting the primary emulsion including the aqueous solution of the bioactive substance and the polymer solution for the carrier dissolved in the solvent into the solution of the polymer having the sol-gel transition property in the aqueous medium to form a secondary emulsion, followed by gelating the secondary emulsion and removing the solvent to collect the microspheres. Further, the solvent having high water solubility may be used through a method of completely gelating the secondary emulsion, and may be used without limitation. Furthermore, the residual solvent and the aqueous medium may be removed at a rapid speed by evaporating the residual solvent and the entire aqueous medium using a vacuum drying method during the removal of the solvent after gelation, and in some cases, the aqueous medium itself may be used by completely drying the aqueous medium without performing a washing process. Further, the size of the particles may be controlled by controlling the concentration of the polymer having the sol-gel transition property included in the aqueous medium, and a stirring process may be omitted. Furthermore, the reaction volume of the particles may be significantly reduced and thus the particles may be easily mass-produced.

BRIEF DESCRIPTION OF DRAWINGS

FIG. 1 is a scanning electron microscope (SEM) photograph of surfaces of microspheres prepared according to Examples 2 and 5 and Comparative Example 2. In this case.

BEST MODE

Hereinafter, the configurations and effects of the present invention will be described in more detail with reference to Examples, but the Examples are merely intended to exemplify the present invention, and the scope of the present invention is not limited to only the Examples.

Example 1

Preparation of Microspheres Containing Leuprolide Acetate Using Gelation of Methyl Cellulose 100 mg of leuprolide acetate was dissolved in 100 μl of distilled water, and then mixed with a polymer solution in which 900 mg of PLGA (Resomer RG502H) was dissolved in 1 mL of ethyl acetate to prepare a primary emulsion. The prepared primary emulsion was dispersed in 20 mL of a distilled water solution containing pre-prepared 10% methyl cellulose using a homogenizer. A secondary emulsion was formed, and then gelated by adding 1 g of NaCl and increasing a temperature to 40° C. The residual solvent and medium were removed for 2 hours under the vacuum condition to prepare solidified microspheres. The prepared microspheres were washed with distilled water several times and then freeze-dried.

Example 2

Preparation of Microspheres Containing Leuprolide Acetate Using Gelation of Methyl Cellulose 90 mg of leuprolide acetate was dissolved in 100 μL of distilled water, and then mixed with a polymer solution in which 810 mg of PLGA (Resomer RG502H) was dissolved in 1 mL of ethyl acetate to prepare a primary emulsion. The prepared primary emulsion was dispersed in 20 mL of a distilled water solution containing pre-prepared 7.5% methyl cellulose using a homogenizer. A secondary emulsion was formed, and then gelated by adding 1 g of NaCl and increasing a temperature to 40° C. The residual solvent and medium were removed for 2 hours under the vacuum condition to prepare solidified microspheres. The prepared microspheres were washed with distilled water several times and then freeze-dried.

Example 3

Preparation of Microspheres Containing Leuprolide Acetate Using Gelation of Methyl Cellulose 160 mg of leuprolide acetate was dissolved in 100 μL of distilled water, and then mixed with a polymer solution in which 640 mg of PLGA (Resomer RG502H) was dissolved in 1 mL of ethyl acetate to prepare a primary emulsion. The prepared primary emulsion was dispersed in 20 mL of a distilled water solution containing pre-prepared 7.5% methyl cellulose using a homogenizer. A secondary emulsion was formed, and then gelated by adding 1 g of NaCl and increasing a temperature to 40° C. The residual solvent and medium were removed for 2 hours under In the vacuum condition to prepare solidified microspheres. The prepared microspheres were washed with distilled water several times and then freeze-dried.

Example 4

Preparation of Microspheres Containing Leuprolide Acetate Using Gelation of Methyl Cellulose 160 mg of leuprolide acetate was dissolved in 150 μL of distilled water, and then mixed with a polymer solution in which 640 mg of PLGA (Lakeshore 5050DLG2A) was dissolved in 1 mL of ethyl acetate to prepare a primary emulsion. The prepared primary emulsion was dispersed in 20 mL of a distilled water solution containing pre-prepared 7.5% methyl cellulose using a homogenizer. A secondary emulsion was formed, and then gelated by adding 1 g of NaCl and increasing a temperature to 40° C. The residual solvent and medium were removed for 2 hours under the vacuum condition to prepare solidified microspheres. The prepared microspheres were washed with distilled water several times and then freeze-dried.

Example 5

Preparation of Microspheres Containing Leuprolide Acetate Using Gelation of Poloxamer 100 mg of leuprolide acetate was dissolved in 100 μL of distilled water, and then mixed with a polymer solution in which 900 mg of PLGA (PLGA5005) was dissolved in 1 mL of ethyl acetate to prepare a primary emulsion. The prepared primary emulsion was dispersed in 20 mL of a distilled water solution containing pre-prepared 18% poloxamer (poloxamer407) using a homogenizer. The secondary emulsion was formed and then gelated by increasing a temperature to 40° C. Thereafter, the residual solvent and medium were removed for 2 hours under the vacuum condition to prepare solidified microspheres. The prepared microspheres were washed with distilled water several times and then freeze-dried.

Example 6

Preparation of Microspheres Containing Leuprolide Acetate Using Gelation of Poloxamer 60 mg of leuprolide acetate was dissolved in 100 μL of distilled water, and then mixed with a polymer solution in which 540 mg of PLGA (Resomer RG502H) was dissolved in 1 mL of ethyl acetate to prepare a primary emulsion. The prepared primary emulsion was dispersed in 20 mL of a distilled water solution containing pre-prepared 18% poloxamer (poloxamer407) using a homogenizer. The secondary emulsion was formed and then gelated by increasing a temperature to 40° C. Thereafter, the residual solvent and medium were removed for 2 hours under the vacuum condition to prepare solidified microspheres. The prepared microspheres were washed with distilled water several times and then freeze-dried.

Example 7

Preparation of Microspheres Containing Leuprolide Acetate Using Gelation of Poloxamer 200 mg of leuprolide acetate was dissolved in 300 μL of distilled water, and then mixed with a polymer solution in which 800 mg of PLGA (Resomer RG503H) was dissolved in 3 mL of ethyl acetate to prepare a primary emulsion. The prepared primary emulsion was dispersed in 20 mL of a distilled water solution containing pre-prepared 20% poloxamer (poloxamer407) using a homogenizer. The secondary emulsion was formed and then gelated by increasing a temperature to 40° C. Thereafter, the residual solvent and medium were removed for 2 hours under the vacuum condition to prepare solidified microspheres. The prepared microspheres were washed with distilled water several times and then freeze-dried.

Comparative Example 1

Preparation of Microspheres Containing Leuprolide Acetate Using Conventional Double Emulsion Method 50 mg of leuprolide acetate was dissolved in 100 μL of distilled water, and then mixed with a polymer solution in which 450 mg of PLGA (Lakeshore 7525DLPLG2A) was dissolved in 1 mL of methylene chloride to prepare a primary emulsion. The prepared primary emulsion was dispersed in 200 mL of a distilled water solution containing pre-prepared 1% polyvinylalcohol (molecular weight of 30,000 to 50,000) using a homogenizer. The secondary emulsion was formed, and then stirred for 2 hours to remove the residual solvent and the aqueous medium. The solidified microspheres were washed with distilled water several times and then freeze-dried.

Comparative Example 2

Preparation of Microspheres Containing Leuprolide Acetate Using Conventional Double Emulsion Method 100 mg of leuprolide acetate was dissolved in 100 μL of distilled water, and then mixed with a polymer solution in which 900 mg of PLGA (Lakeshore 7525DLPLG2A) was dissolved in 1 mL of methylene chloride to prepare a primary emulsion. The prepared primary emulsion was dispersed in 350 mL of a distilled water solution containing pre-prepared 1% polyvinylalcohol (molecular weight of 30,000 to 50,000) using a homogenizer. The secondary emulsion was formed, and then stirred for 2 hours to remove the residual solvent and the aqueous medium. The solidified microspheres were washed with distilled water several times and then freeze-dried.

Comparative Example 3

Preparation of Microspheres Containing Leuprolide Acetate Using Ethyl Acetate as Polymer Solvent When microspheres was prepared with ethyl acetate by the methods of Comparative Examples 1 and 2, the spherical particles were not formed, and the encapsulation ratio was less than 10%. As a result, it was seen that the microspheres were not prepared by the conventional double emulsion method. Accordingly, in order to prepare the microspheres with ethyl acetate, a multistep method of forming microspheres was used in this Comparative Example. 50 mg of leuprolide acetate was dissolved in 100 μL of distilled water, and then mixed with a polymer solution in which 500 mg of PLGA (Lakeshore 7525DLPLG2A) was dissolved in 1 mL of methylene chloride to prepare a primary emulsion. The prepared primary emulsion was dispersed in 6 mL of a distilled water solution containing pre-prepared 1% polyvinylalcohol (molecular weight of 30,000 to 50,000) and 10% NaCl using a homogenizer. The formed secondary emulsion was added into 10 mL of a distilled water solution containing 1% polyvinylalcohol and 10% NaCl to form a tertiary emulsion, and the tertiary emulsion was added into 200 mL of distilled water containing 1% polyvinylalcohol and 10% NaCl and stirred for 3 hours. The solidified microspheres were washed with distilled water several times and then freeze-dried.

The components and contents of the microspheres prepared in Examples 1 to 7 and Comparative Examples 1 and 2 are summarized in the following Table 1.

TABLE 1

| Classification | Conc. of PLGA (mg/mL) | Solvent for PLGA | Added amount of API (wt %) | Solvent for API (DW, v/v) | Surfactant in aqueous medium | Conc. of surfactant (%) | Volume of aqueous medium (mL) |
|---|---|---|---|---|---|---|---|
| Example 1 | 900 | Ethyl acetate | 10 | 10 | Methyl cellulose | 10 | 20 |
| Example 2 | 810 | Ethyl acetate | 10 | 10 | Methyl cellulose | 7.5 | 20 |
| Example 3 | 640 | Ethyl acetate | 20 | 10 | Methyl cellulose | 7.5 | 20 |
| Example 4 | 640 | Ethyl acetate | 20 | 15 | Methyl cellulose | 7.5 | 20 |
| Example 5 | 900 | Ethyl acetate | 10 | 15 | poloxamer | 18 | 20 |
| Example 6 | 540 | Ethyl acetate | 10 | 10 | poloxamer | 18 | 20 |
| Example 7 | 800 | Ethyl acetate | 20 | 10 | poloxamer | 20 | 20 |
| Comparative Example 1 | 450 | Methylene chloride | 10 | 10 | Poly(vinyl alcohol) | 1 | 200 |
| Comparative Example 2 | 900 | Methylene chloride | 10 | 10 | Poly(vinyl alcohol) | 1 | 350 |
| Comparative Example 3 | 500 | Ethyl acetate | 10 | 10 | Poly(vinyl alcohol) | 1 | 200 |

Experimental Example 1

Determination of Surface Shapes of Microspheres Containing Leuprolide Acetate

Figure 1A:
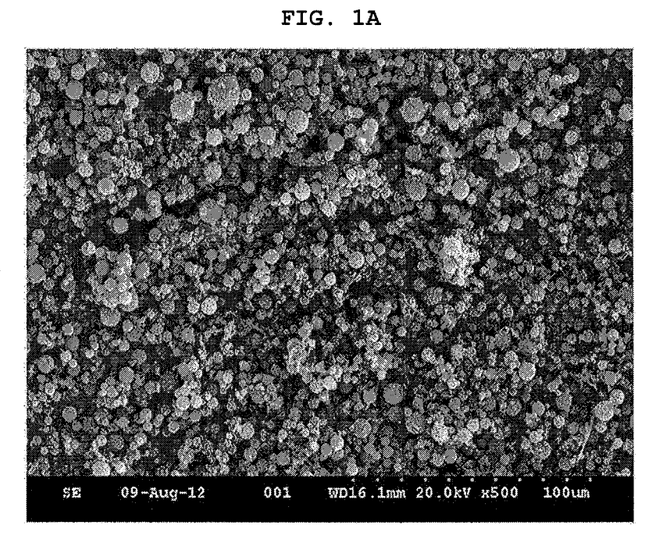
FIG. 1A represents microspheres using methyl cellulose of Example 2.
Figure 1B:
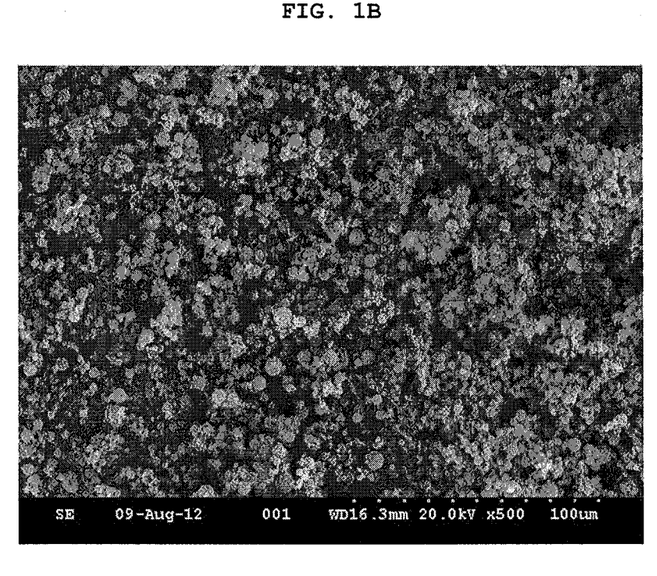
FIG. 1B represents microspheres using poloxamer of Example 5.
Figure 1C:
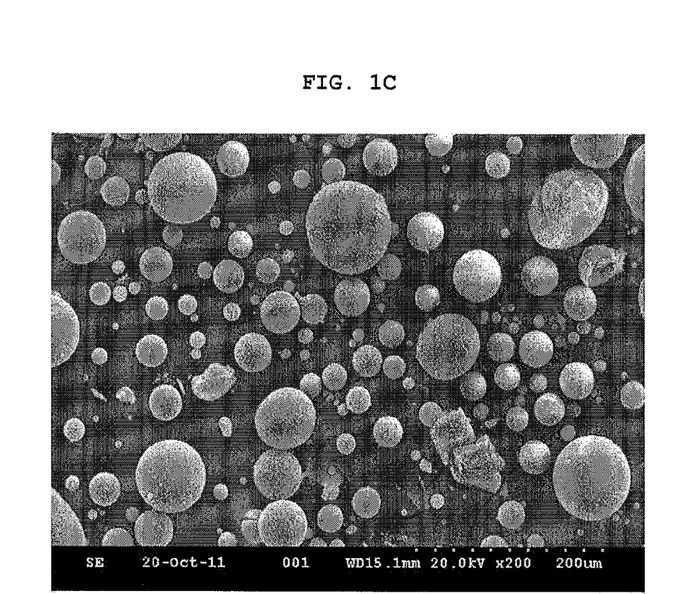
FIG. 1C represents microspheres of Comparative Example 2.

The surfaces of the microspheres prepared in Examples 2 and 5 and Comparative Example 2 were observed under a scanning electron microscope (SEM). The measured results are illustrated in FIGS. 1A, 1B, and 1C, respectively.

From the measurement results, it was seen that the microspheres of Examples 2 and 5 using gelation of methyl cellulose and poloxamer had a relatively smooth surface due to small porosity of the surfaces of the microspheres, and showed uniform particle size distribution. In comparison, in the case of the microspheres prepared by the conventional double emulsion method using poly(vinyl alcohol), the porosity of the surface was observed, there surfaces were uneven, and large particles having irregular shapes were observed.

Meanwhile, it was seen that the microspheres prepared according Examples 1 and 5 had small particle sizes, compared to the microspheres prepared according Examples 2, 3, and 4 (not shown).

Experimental Example 2

Measurement of Encapsulation Amount of Leuprolide Acetate of Microspheres

For the encapsulation ratio of the drug, a predetermined amount of the microspheres was fully dissolved in dimethyl sulfoxide (DMSO) and then filtered through a syringe filter to be used a test liquid, and a content of the drug which was encapsulated in the microspheres was measured using HPLC. In this case, for HPLC analysis, C18 column (150 mm L.×4.6 mm I.D. 5 µm) and Gemini-NX C18 column (4.0 mm L.×3.0 mm I.D.) were used. A solvent and a mobile phase of a sample were aqueous solutions (pH 7.0) of potassium carbonate and 25% acetonitrile (ACN), and detected at UV 220 nm.

The contents of the drugs in the prepared microspheres was measured to determine encapsulation ratios. Then, the encapsulation ratios are listed in the following Table 2.

TABLE 2

| Classification | Drug encapsulation ratio (wt %) |
| --- | --- |
| Example 1 | 79.8 |
| Example 2 | 89.3 |
| Example 3 | 88.0 |
| Example 4 | 100.0 |
| Example 5 | 83.6 |
| Example 7 | 83.6 |
| Comparative Example 1 | 99 |
| Comparative Example 2 | 45.3 |
| Comparative Example 3 | 30 |

As described in Table 2, it was seen that most of the microsphere formulation of the present invention had a drug encapsulation ratio of 70 to 100 wt % even when ethyl acetate which was a solvent having high water solubility was used to dissolve a polymer carrier. On the other hand, when the polymer having the sol-gel transition property according to the present invention was not used, it was seen that the microspheres showed a drug encapsulation efficiency in the range of 45 to 99.5 wt % when methylene chloride which was a solvent having high toxicity was used, but a drug encapsulation ratio of not more than 30 wt % when ethyl acetate was used.

Experimental Example 3

In-Vitro Release Test of Microspheres Containing Leuprolide Acetate

An in-vitro release test of microspheres containing leuprolide acetate of the present invention was performed below.

Figure 2:
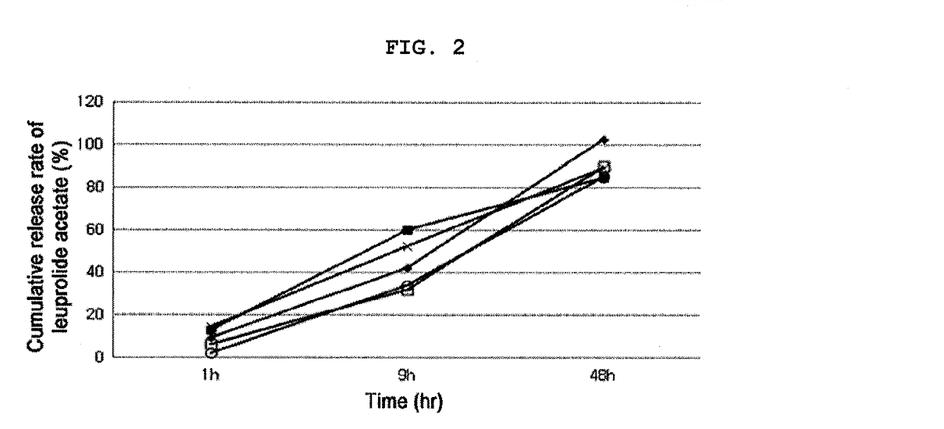
FIG. 2 is a graph illustrating an in-vitro release test result of the microspheres prepared according to Examples 1 to 5. In this case, ▲ represents microspheres of Example 1, □ represents microspheres of Example 2, ○ represents microspheres of Example 3, ♦ represents microspheres of Example 4, and ■ represents microspheres of Example 5.

First, 1000 mL of a test solution was prepared by putting 200 mL of 0.1 mol/L lactic acid, 5 mL of 20 (w/v) % polysorbate 80, and 200 mL of 2 (w/v) % poly(vinyl alcohol) (PVA) into the same container and adding distilled water. Next, 100 mg of the prepared microspheres was put into a 120 mL glass test tube, and 100 mL of the test solution was added thereto. Thereafter, the container was sealed with a rubber cap, and the resulting mixture was immediately shaken and mixed. Then, the container was closed with an aluminum cap. 1 mL of each suspension was extracted using a glass syringe provided with a needle with 23 gauge after 1, 9, and 48 hours while being incubated at 48±0.5° C. Next, a supernatant obtained by centrifugation was immediately used as the test liquid and analyzed with HPLC, and the drug-release results are listed in Table 3 and shown in FIG. 3.

TABLE 3

| Time | Example 1 | Example 2 | Example 3 | Example 4 | Example 5 | Comparative Example 1 | Comparative Example 2 |
| --- | --- | --- | --- | --- | --- | --- | --- |
| 1 hour | 14.9 | 6.3 | 2.1 | 9.3 | 13.1 | 9.6 | 10.4 |
| 9 hours | 52.8 | 32.3 | 34.2 | 42.4 | 60.4 | 33.4 | 39.7 |
| 48 hours | 89.6 | 90.0 | 85.3 | 102.7 | 85.1 | 87.1 | 88.4 |

The release rate (%) varied according to various complex factors, but generally, the faster the diffusion rate of drugs and the smaller the particle size (since smaller particles have greater surface area than large particles at the same weight), the faster the particles would release the drugs.

As listed in Table 3, it could be seen that the microspheres prepared according to the present invention had an entire release ratio of 85% or more, which indicated that the microspheres of Examples showed a similar release behavior to the microspheres of Comparative Examples despite the high drug encapsulation amount.

The invention claimed is:

1. A method of preparing microspheres, in which a bioactive substance is encapsulated in a polymer for a carrier, comprising:
   1) forming a secondary emulsion by injecting a primary emulsion, in which the bioactive substance and the polymer for a carrier are mixed, into an aqueous medium in which a polymer having a sol-gel transition property is dissolved (Step 1);
   2) performing a gelation reaction on the secondary emulsion (Step 2); and
   3) removing a residual solvent and an aqueious medium without stirring, and collecting the microspheares after step 2 (Step 3).

2. The method of preparing microspheres of claim 1, wherein the bioactive substance is at least one selected from the group consisting of luteinizing hormone-release hormone (LHRH) homologs, peptides, and salts thereof.

3. The method of preparing microspheres of claim 2, wherein the bioactive substance is at least one selected from the group consisting of goserelin, leuprolide acetate, triptorelin, buserelin, nafarelin, cetrorelix, and argitide.

4. The method of preparing microspheres of claim 1, wherein the primary emulsion is prepared by dissolving the polymer for the carrier in at least one solvent selected from the group consisting of methylene chloride, chloroform, acetonitrile, dimethylsulfoxide, dimethylformamide, and ethyl acetate.

5. The method of preparing microspheres of claim 1, wherein the polymer for the carrier is a biodegradable polymer.

6. The method of preparing microspheres of claim 5, wherein the polymer for the carrier is at least one selected from the group consisting of polylactide, polyglycolide, and poly(lactide-co-glycolide).

7. The method of preparing microspheres of claim 1, wherein the polymer having the sol-gel transition property is at least one selected from the group consisting of methyl cellulose, hydroxypropylmethylcellulose (HPMC), ethylhydroxyethylcellulose (EHEC), xyloglucan, chitosan, poly(N-isopropylamide) (PNIPAM), poly(N-isopropylamide-co-acrylic acid), poloxamer (PEO-PPO-PEO), Poloxamer-g-PAA, PAA-g-poloxamer, PEO-PLGA-PEO, and poly(vinyl alcohol).

8. The method of preparing microspheres of claim 1, wherein the removal of the residual solvent and the aqueous medium of Step 3) are performed by evaporating the residual solvent and the aqueous medium under a vacuum in the range of 0 to 0.99 Torr.

9. Microspheres comprising a bioactive substance encapsulated in the polymer for a carrier, prepared by the method of claim 1.

10. A drug delivery system comprising the microspheres of claim 9 as an active component.

11. The drug delivery system of claim 10, wherein the drug delivery system is in the form of an injection.

* * * * *